(12) United States Patent
Foster

(10) Patent No.: US 11,357,665 B2
(45) Date of Patent: *Jun. 14, 2022

(54) CEREBRAL PROTECTION SYSTEM

(71) Applicant: Jeffrey Foster, Orange Village, OH (US)

(72) Inventor: Jeffrey Foster, Orange Village, OH (US)

( * ) Notice: Subject to any disclaimer, the term of this patent is extended or adjusted under 35 U.S.C. 154(b) by 843 days.

This patent is subject to a terminal disclaimer.

(21) Appl. No.: 16/134,258

(22) Filed: Sep. 18, 2018

(65) Prior Publication Data

US 2019/0015249 A1 Jan. 17, 2019

Related U.S. Application Data

(63) Continuation-in-part of application No. 14/774,599, filed as application No. PCT/US2014/023579 on Mar. 11, 2014, now Pat. No. 10,076,440.

(60) Provisional application No. 61/779,930, filed on Mar. 13, 2013.

(51) Int. Cl.
| | |
|---|---|
| A61F 7/10 | (2006.01) |
| A61F 7/03 | (2006.01) |
| A61F 7/00 | (2006.01) |
| A61F 7/02 | (2006.01) |

(52) U.S. Cl.
CPC ............... *A61F 7/106* (2013.01); *A61F 7/03* (2013.01); *A61F 2007/0002* (2013.01); *A61F 2007/0007* (2013.01); *A61F 2007/0008* (2013.01); *A61F 2007/0009* (2013.01); *A61F 2007/0015* (2013.01); *A61F 2007/023* (2013.01); *A61F 2007/0228* (2013.01); *A61F 2007/0238* (2013.01); *A61F 2007/0249* (2013.01); *A61F 2007/0276* (2013.01); *A61F 2007/0282* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,643,665 | A | * | 2/1972 | Caillouette ............. F24V 30/00 607/114 |
| 4,138,743 | A | * | 2/1979 | Elkins .................... A42B 3/285 2/171.2 |
| 4,382,446 | A | | 5/1983 | Truelock |
| 4,552,149 | A | | 11/1985 | Tatsuki |

(Continued)

FOREIGN PATENT DOCUMENTS

| | | |
|---|---|---|
| WO | WO 02/34177 A1 | 5/2002 |
| WO | WO 2011/015821 A1 | 2/2011 |

*Primary Examiner* — Joseph A Stoklosa
*Assistant Examiner* — Adam J Avigan
(74) *Attorney, Agent, or Firm* — Fay Sharpe LLP

(57) ABSTRACT

A cerebral protection system generally includes an array of cold packs, an insulating cover, and optionally a set of trays. The cold pack contains two reactive materials separated by a rupturable membrane. When the first reactive material and the second reactive material are mixed, an endothermic reaction occurs. The system can be used to induce hypothermia in selected regions of the brain when used. The system can be used to treat conditions including concussion, traumatic brain injury (TBI), heatstroke, cardiac arrest, respiratory arrest, anoxic brain injury, ischemic stroke, transient ischemic attack (TIA), or hypoxic ischemic encephalopathy.

14 Claims, 22 Drawing Sheets

(56) References Cited

U.S. PATENT DOCUMENTS

| | | | | |
|---|---|---|---|---|
| 4,765,338 | A | * | 8/1988 | Turner ...................... A61F 7/02 |
| | | | | 607/110 |
| 5,129,391 | A | | 7/1992 | Brodsky |
| 5,261,399 | A | * | 11/1993 | Klatz ........................ A61F 7/10 |
| | | | | 607/104 |
| 5,539,934 | A | * | 7/1996 | Ponder ................... A42B 3/285 |
| | | | | 2/413 |
| 2008/0184456 | A1 | | 8/2008 | Fontanez |
| 2009/0198311 | A1 | | 8/2009 | Johnson et al. |

\* cited by examiner

CEREBRAL PROTECTION SYSTEM

RELATED APPLICATION

This application is a continuation-in-part of U.S. patent application Ser. No. 14/774,599, filed Sep. 10, 2015, now U.S. Pat. No. 10,076,440, which is a 371 of PCT Application No. PCT/US2014/023579, filed Mar. 11, 2014, which claims priority from U.S. Provisional Application Ser. No. 61/779,930 which was filed on Mar. 13, 2013. The entirety of that application is incorporated hereinto by reference.

BACKGROUND

The present disclosure relates to systems and methods for protecting the cerebral system. The systems and methods involve the production of selective cerebral hypothermia to the brain to reduce injury.

Hypothermia is a condition that occurs when a body loses heat faster than it can produce heat, thereby causing a reduced body temperature. In humans, normal body temperature is around 98.6° F. (37° C.). Hypothermia may occur as the body temperature passes below about 95° F. (35° C.).

Hypothermia is considered to be a medical emergency because the heart, nervous system, and other organs do not function normally. However, hypothermia is also a useful medical technique. Temperature reduction reduces metabolic activity, which can provide vital time to transport and treat patients. Cooling systems designed for use in hospitals may cost in the range of $20,000 to $30,000 and have maintenance costs.

Hospitals that use hypothermia target treatment within 6 hours of injury because such treatments have increased survival 23% to 48% according to studies. It is desirable to begin treatment as early as possible.

Emergency medical services (EMS) units typically pick up patients and take them to the nearest hospital for treatment. Some EMS units carry iced saline to infuse patients while in transport to the hospital. Such infusions do provide a reduction in patient temperature, but also have potentially deleterious effects including hemoglobin reduction, fluid overload, and time for IV insertion.

It would be desirable to develop new systems and methods for reducing the likelihood and/or amount of damage caused by brain injuries shortly after a patient has suffered an injury.

BRIEF DESCRIPTION

The present disclosure relates to cerebral protection systems and methods. The systems and methods are suitable for in-field generation of selective hypothermia.

Disclosed in embodiments is a cerebral protection system which includes a first array of cold packs shaped to cover a first portion of a head and a second array of cold packs shaped to cover a second portion of the head. The first array includes one or more first cold packs. Each first cold pack contains a first reactive material, a second reactive material, and a first rupturable membrane separating the first reactive material from the second reactive material. The second array includes one or more second cold packs. Each second cold pack contains the first reactive material, the second reactive material, and a second rupturable membrane isolating the first reactive material from the second reactive material. The first reactive material and the second reactive material are capable of reacting in an endothermic reaction when in contact.

In some embodiments, the first rupturable membrane and the second rupturable membrane can be ruptured independently.

The first reactive material may be water and the second reactive material may be ammonium chloride.

Optionally, the cerebral protection system further includes two earholes.

In some embodiments, the cerebral protection further includes an insulating cover.

The cerebral protection system may further include a neck fastener shaped to extend from a first side of a front of a neck to a second side of the front of the neck.

Optionally, the cerebral protection system further includes a chin fastener shaped to extend from a first area adjacent a first cheek of the head below a chin of the head to a second area adjacent a second cheek of the head.

Disclosed in other embodiments is a cerebral protection system that includes a first array of cold packs shaped to cover a top, left portion of a head, a second array of cold packs shaped to left cheek and above-left ear portions of the head, a third array of cold packs shaped to cover left neck and below-left ear portions of the head, a fourth array of cold packs shaped to cover a top, right portion of the head, a fifth array of cold packs shaped to cover right cheek and above-right ear portions of the head, and a sixth array of cold packs shaped to cover right neck and below-right ear portions of the head.

The first array includes one or more first cold packs. Each first cold pack contains a first reactive material, a second reactive material, and a first rupturable membrane separating the first reactive material from the second reactive material.

The second array includes one or more second cold packs, each second cold pack containing the first reactive material, the second reactive material, and a second rupturable membrane isolating the first reactive material from the second reactive material.

The third array includes one or more third cold packs, each third cold pack containing the first reactive material, the second reactive material, and a third rupturable membrane isolating the first reactive material from the second reactive material.

The fourth array includes one or more fourth cold packs, each fourth cold pack containing the first reactive material, the second reactive material, and a fourth rupturable membrane isolating the first reactive material from the second reactive material.

The fifth array includes one or more fifth cold packs, each fifth cold pack containing the first reactive material, the second reactive material, and a fifth rupturable membrane isolating the first reactive material from the second reactive material.

The sixth array includes one or more sixth cold packs, each sixth cold pack containing the first reactive material, the second reactive material, and a sixth rupturable membrane isolating the first reactive material from the second reactive material.

The first reactive material and the second reactive material are capable of reacting in an endothermic reaction when in contact.

In some embodiments, the first rupturable membrane, the second rupturable membrane, the third array rupturable membrane, the fourth array rupturable membrane, the fifth rupturable membrane, and the sixth rupturable membrane can be independently ruptured.

The first reactive material can be water and the second reactive material can be ammonium chloride.

Optionally, the cerebral protection system includes a chin fastener. The chin fastener includes a first portion attached to the second array and a second portion attached to the fifth array.

In some embodiments, the cerebral protection system further includes a neck fastener. The neck fastener includes a first portion attached to the third array and a second portion attached to the sixth array.

The cerebral protection system may further include a first earhole between the second array and the third array; and a second earhole between the fifth array and the sixth array.

Optionally, the cerebral protection system further includes an insulating cover located external to the first array, the second array, the third array, the fourth array, the fifth array, and the sixth array.

The cerebral protection system may further include front neck tabs and rear neck tabs.

In some embodiments, the cerebral protection system further includes a rear slit and a rear fastener for accommodating a ponytail extending from the head.

Optionally, the first array and the fourth array each have four cold packs and the second array, the third array, the fifth array, and the sixth array each have three cold packs.

Disclosed in further embodiments is a cerebral protection system including a first compartment containing a first reactive material, a second compartment containing a second reactive material, and a rupturable membrane separating the first compartment from the second compartment and isolating the first reactive material from the second reactive material. The second reactive material is capable of reacting in an endothermic reaction with the first reactive material when contacted with the first reactive material. The first compartment is shaped to at least partially cover the top of a head. The second compartment is shaped to at least partially cover a back of the head and a neck.

The first reactive material may be water and the second reactive material may be ammonium chloride.

Optionally, the cerebral protection system further includes an insulating cover.

In some embodiments, the first compartment includes a forehead protrusion shaped to at least partially cover the area between eyes of a patient.

The second compartment may include an adjustable neck flap.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
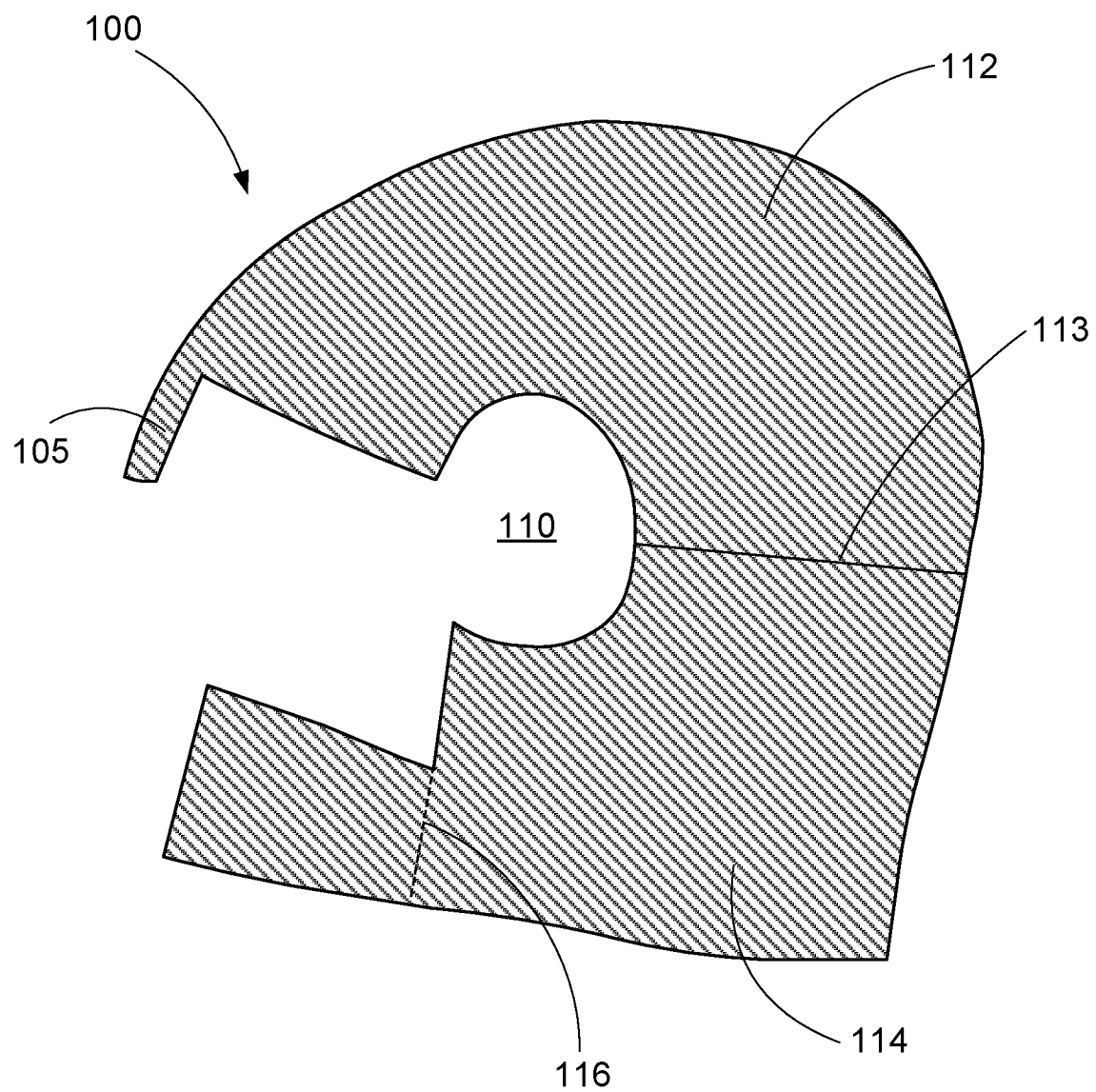
FIG. 1 is a side view of a first exemplary embodiment of a cerebral protection system of the present disclosure.
Figure 2A:
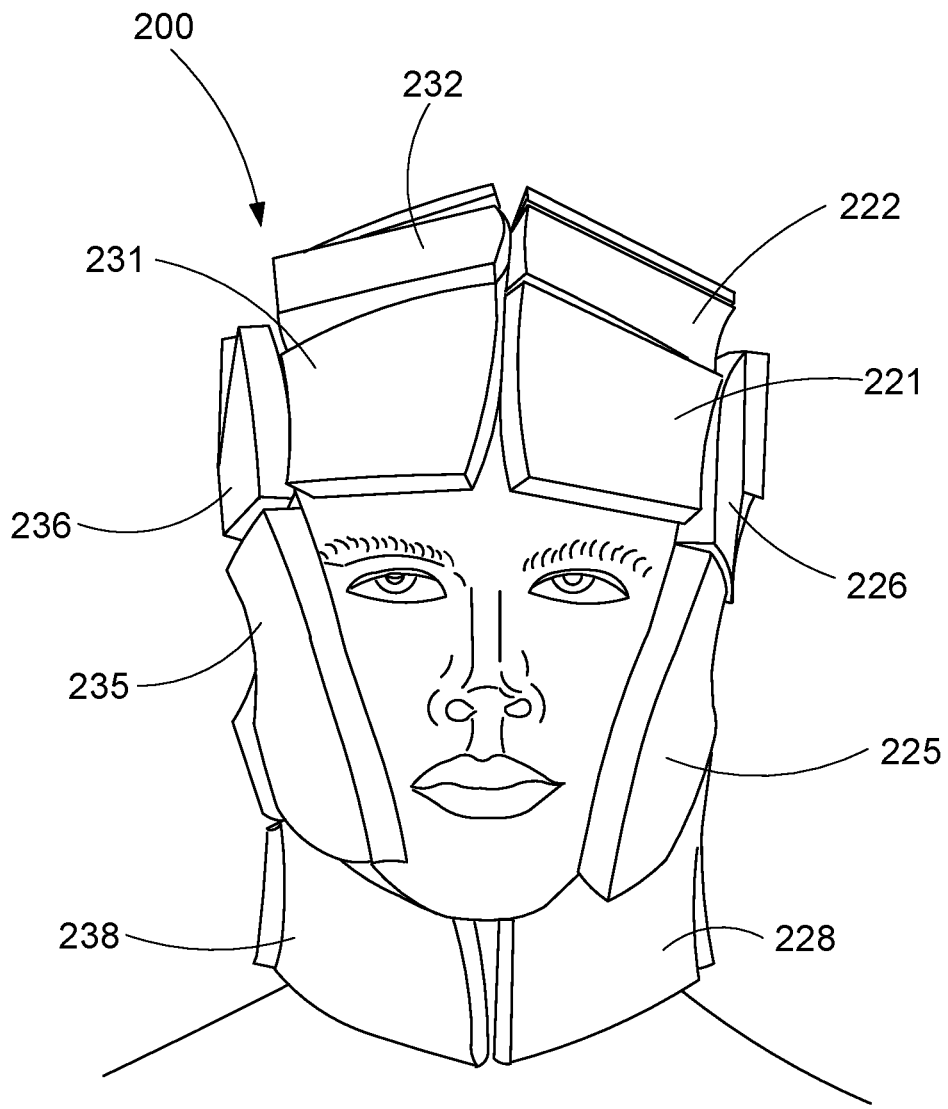
FIGS. 2A-2E are front, front perspective, side, rear perspective, and rear views, respectively, of a second exemplary embodiment of a cerebral protection system of the present disclosure without a cover.
Figure 2B:
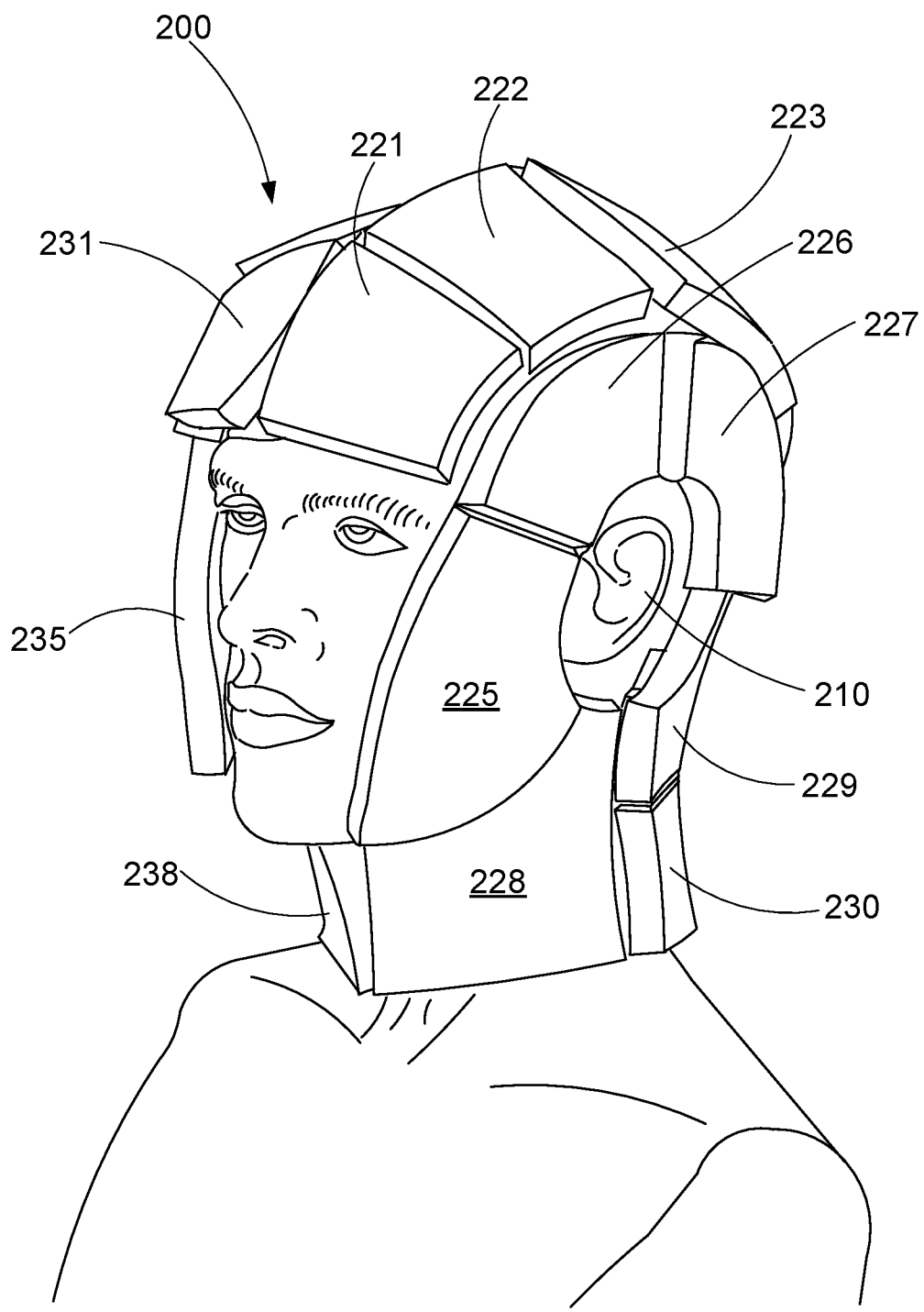
Figure 2C:
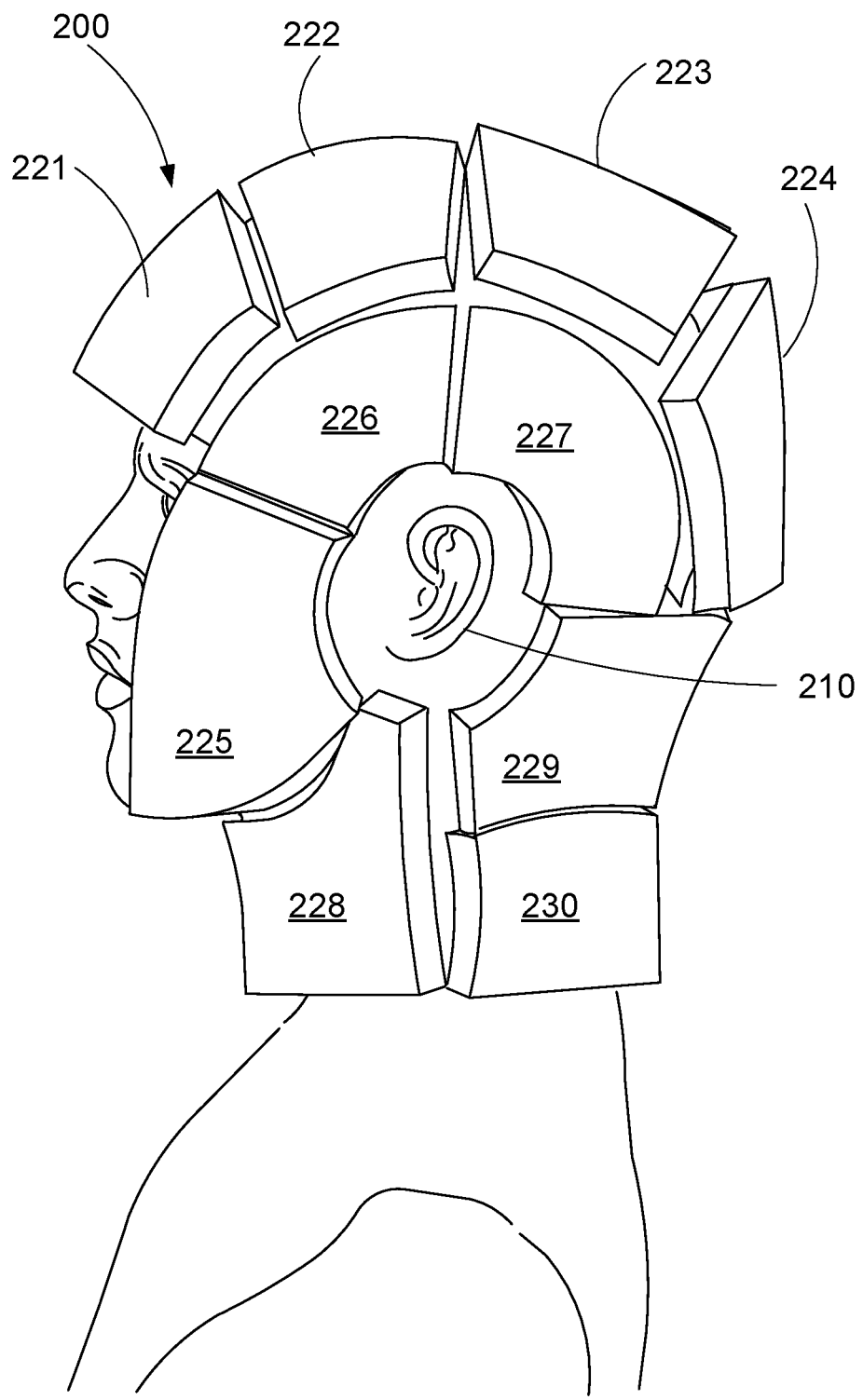
Figure 2D:
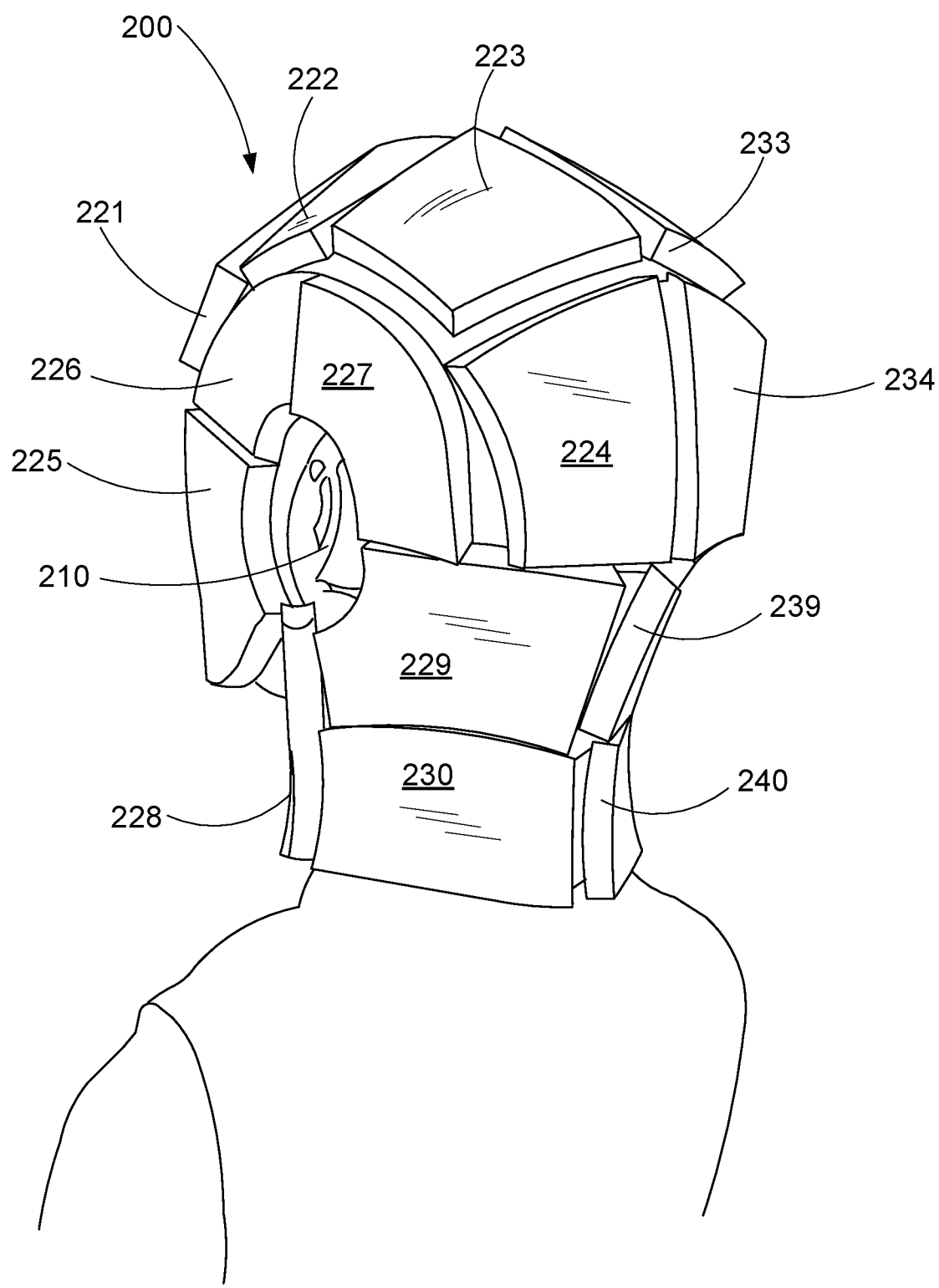
Figure 2E:
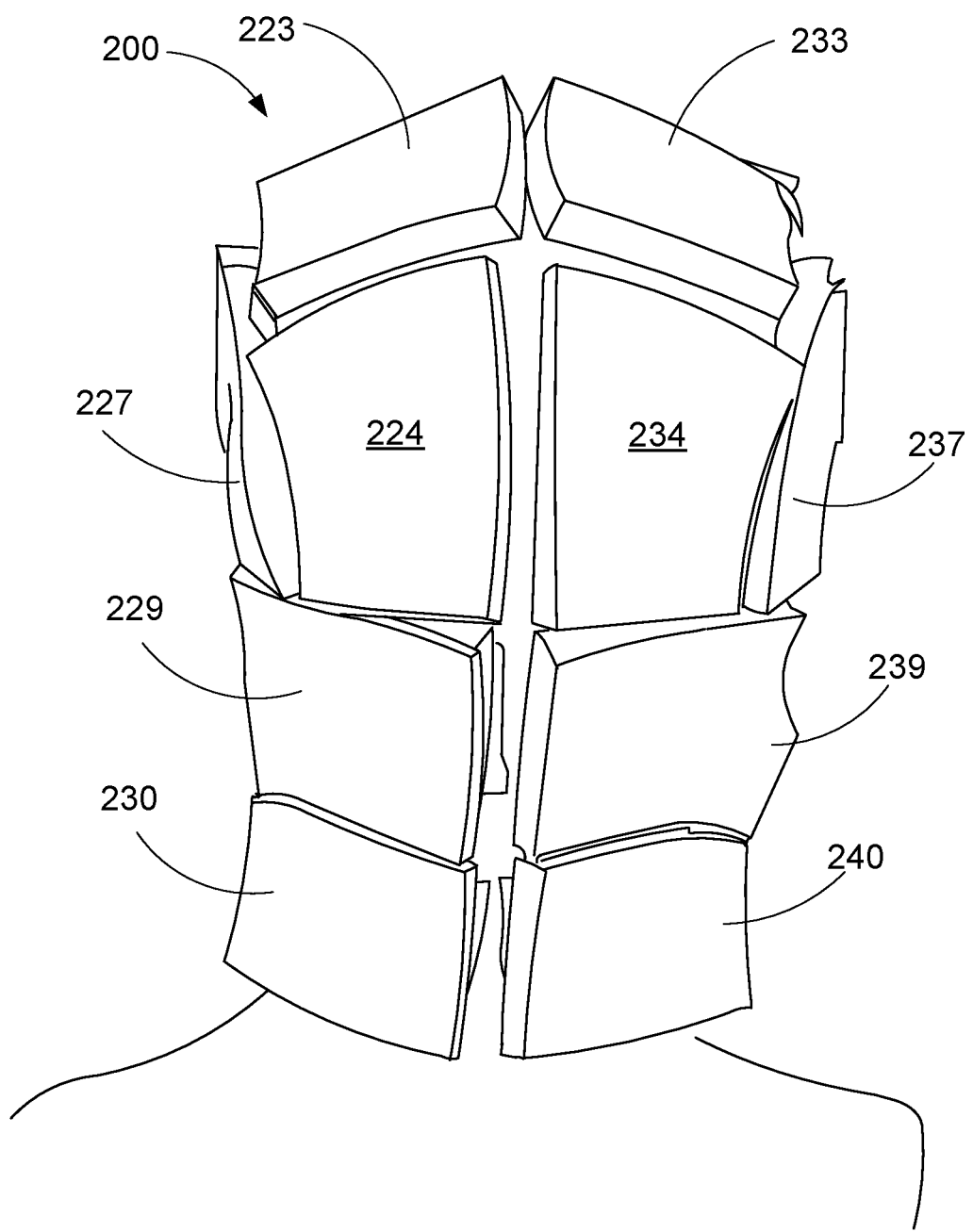

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

Numerical values in the specification and claims of this application should be understood to include numerical values which are the same when reduced to the same number of significant figures.

All ranges disclosed herein are inclusive of the recited endpoint and independently combinable (for example, the range of "from 2 grams to 10 grams" is inclusive of the endpoints, 2 grams and 10 grams, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

FIG. 1 illustrates a side view of an exemplary embodiment of a cerebral protection system 100 of the present disclosure. The cerebral protection system 100 includes an upper portion 112, a lower portion 114, and a rupturable membrane 113 separating the upper portion 112 from the lower portion 114. The cerebral protection system 100 includes earholes 110. The upper portion 112 optionally includes a forehead protrusion 105 which is designed to extend into the area between the eyes. The lower portion 114 includes a neck flap 116 which may be opened to apply the cerebral protection system 100 to a person and tightened or loosened for a good fit. Optionally, the cerebral protection system further includes an insulating cover (not shown here).

The upper portion 112 includes an upper compartment which contains a first reactive material. The lower portion 114 includes a lower compartment which contains a second reactive material. The first reactive material and the second reactive material react endothermically when in contact. The rupturable membrane 113 prevents mixing of the first reactive material and the second reactive material until the membrane 113 is ruptured. The membrane may be ruptured before or after the cerebral protection system 100 is placed on the human, though generally it is before placement. Upon rupture of the membrane 113, the first and second reactive materials are mixed and react endothermically. The endothermic reaction absorbs heat, thereby cooling the brain.

In other embodiments, the cerebral protection system of the present disclosure comprises a set of cold packs shaped to cover a human head, an insulating cover surrounding the set of cold packs, and optionally a set of trays for holding the cold packs. FIGS. 2A-E show one arrangement of the cold packs of the cerebral protection system 200. The insulating cover is not shown in this set of pictures. Visible in these pictures are earholes 210 and a total of 20 cold packs 221-240, including 10 left-side cold packs 221-230 and 10 right-side cold packs 231-240.

The 10 left-side cold packs 221-230 are arranged in three arrays. The first array is shaped to cover a top, left portion of the head and includes four cold packs 221, 222, 223, and 224. The second array is shaped to cover left cheek and above-left ear portions of the head and includes three cold packs 225, 226, and 227. The third array is shaped to cover left neck and below-left ear portions of the head and includes three cold packs 228, 229, and 230.

The 10 right-side cold packs 231-240 are also arranged in three arrays. The fourth array is shaped to cover a top, right portion of the head and includes four cold packs 231, 232, 233, and 234. The fifth array is shaped to cover right cheek and above-right ear portions of the head and includes three cold packs 235, 236, and 237. The sixth array is shaped to cover right neck and below-right ear portions of the head and includes three cold packs 238, 239, and 240.

FIGS. 3A-3E illustrate the cerebral protection system 300 with the insulating cover 345. The cerebral protection system includes an insulating cover 345 which reduces/eliminates heat transfer from the external environment into the cerebral protection system 300. As seen here, the insulating cover surrounds the cold packs (not shown), which are within the interior of the insulating cover. The cover 345 itself may include an outer layer and an inner, insulating layer, the inner layer contacting the cold packs or the set of trays. The outer layer may be relatively thin. In some embodiments, the cover is formed from a plurality of panels. Each panel may be sized and shaped to cover a given array of cold packs, such as the arrays referred to in FIG. 2A-2E above.

The cover 345 includes left cheek cover portion 349, left top cover portion 350, left neck cover portion 351, right cheek cover portion 359, right top cover portion 360, and right neck cover portion 361. The cerebral protection system 300 further includes ear holes 310, a chin fastener 347, a front neck fastener 353, and a rear neck fastener 355. The fasteners 347, 353, 355 are adjustable to permit easy application and removal of the cerebral protection system 300. The fasteners 347, 353, 355 also permit a better fit by securing the cold packs in appropriate locations relative to the head. In this regard, the cold packs can be attached to the interior of the insulating cover using fasteners, without using the set of trays.

Figure 3A:
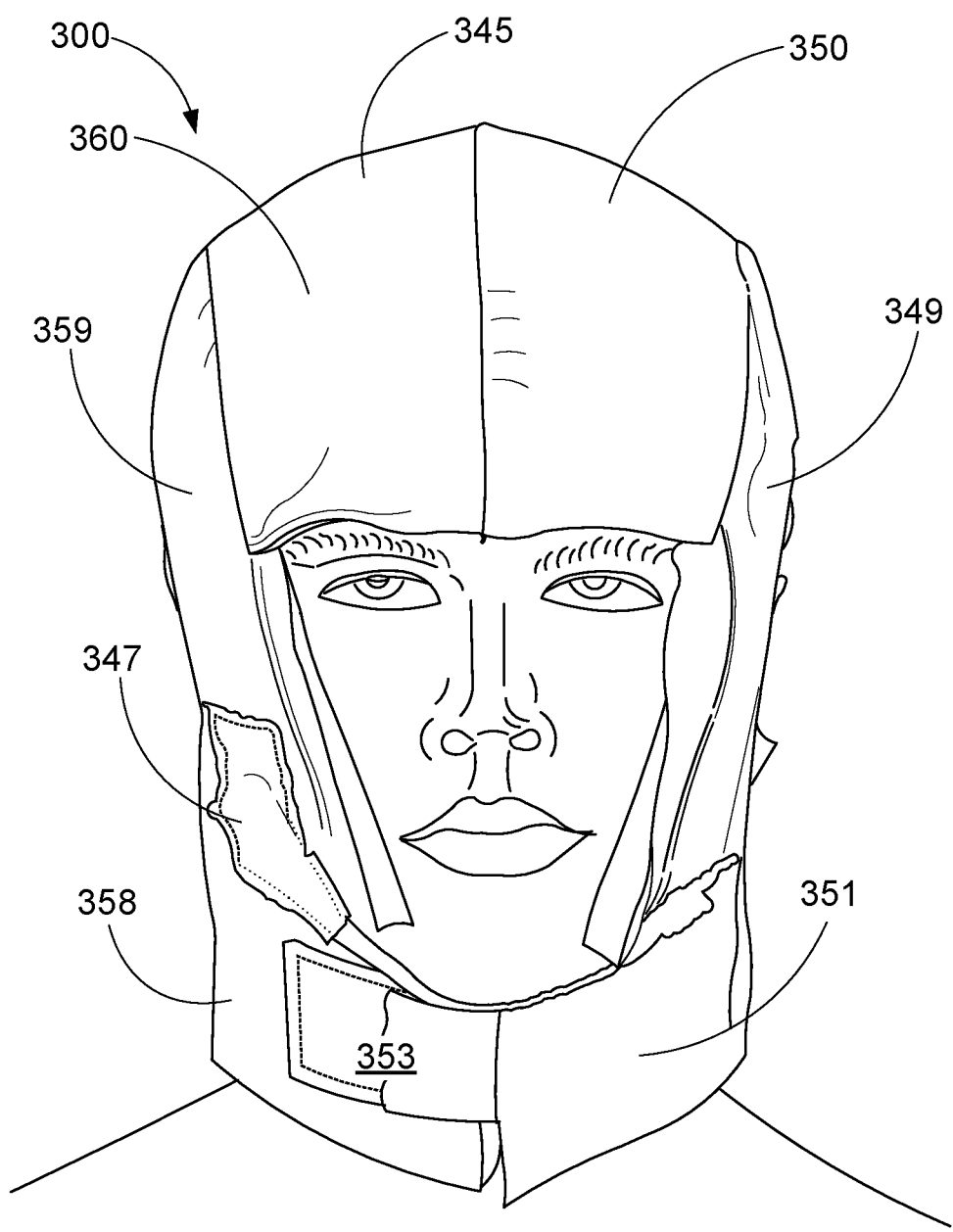
FIG. 3A-E are front, front perspective, side, rear perspective, and rear views, respectively, of an embodiment of a cerebral protection system of the present disclosure with a cover.
Figure 3B:
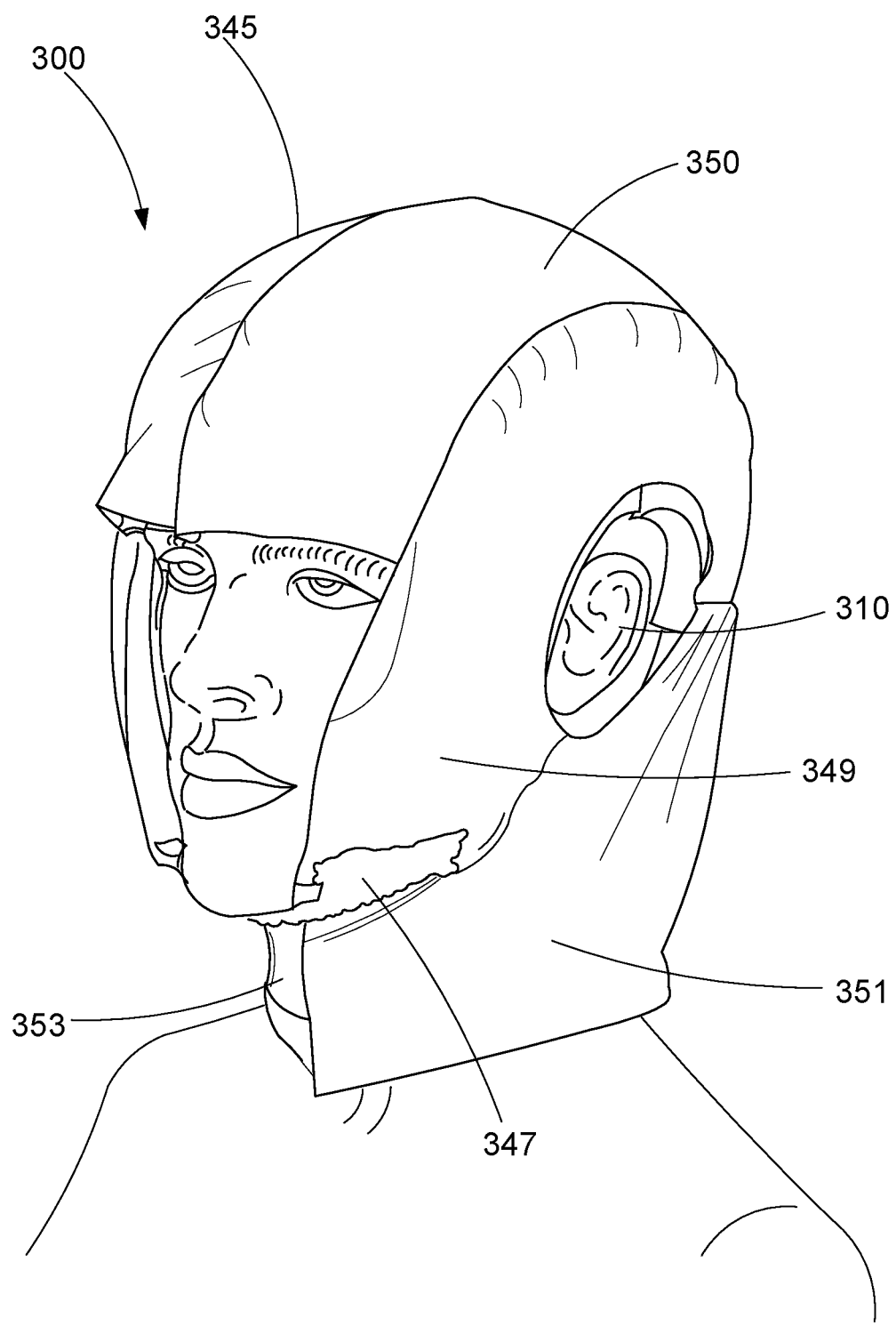
Figure 3C:
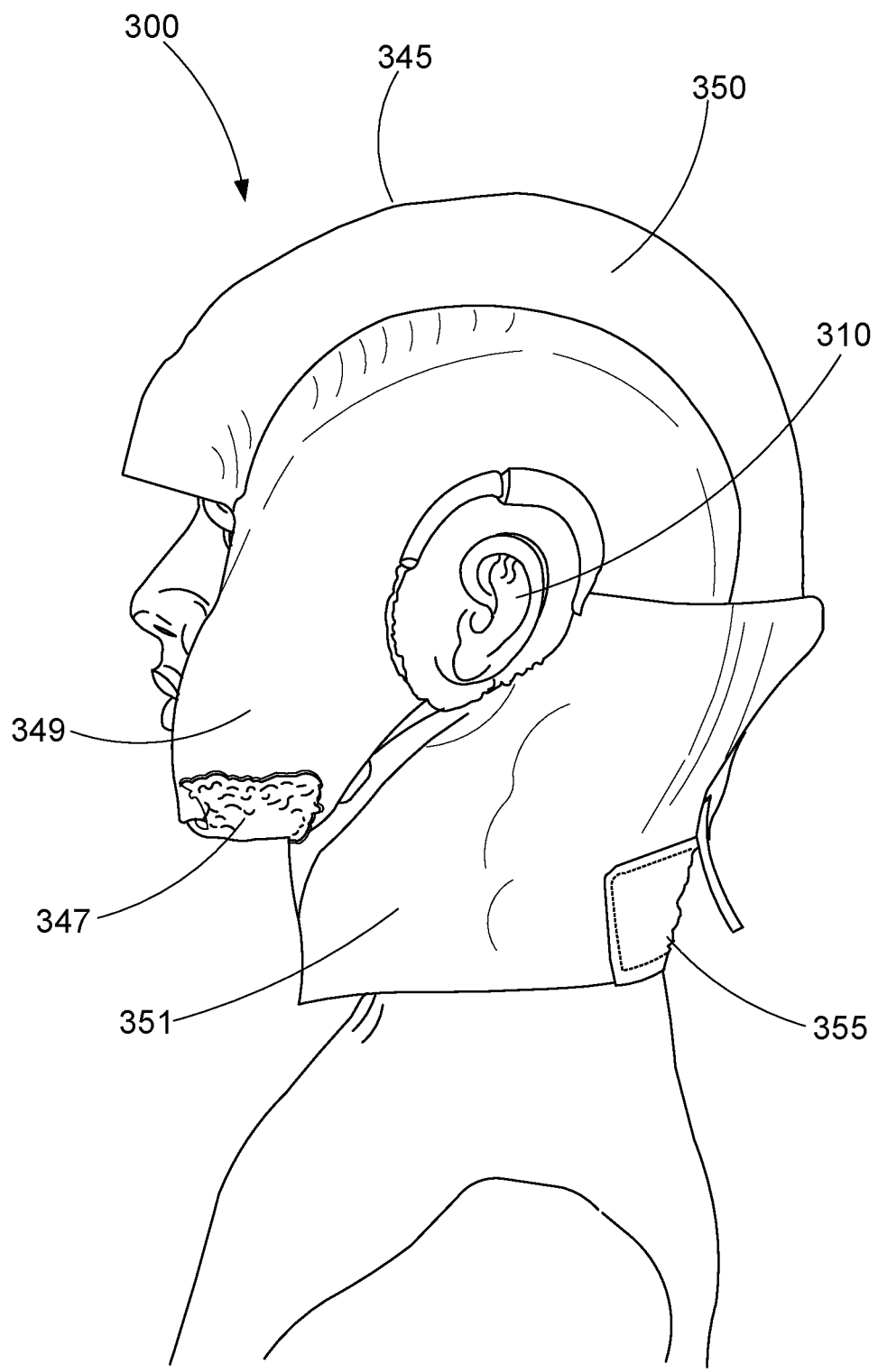
Figure 3D:
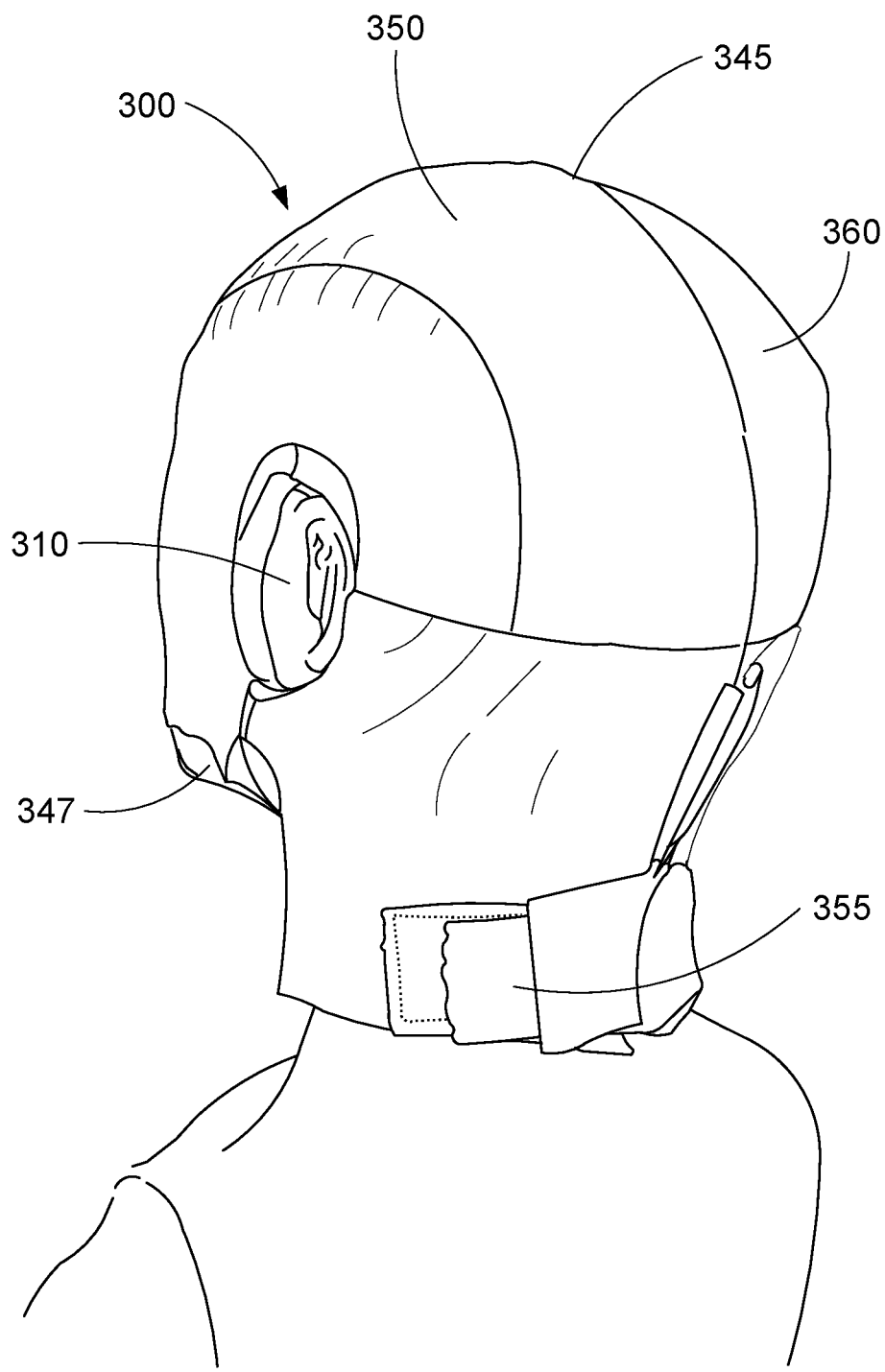
Figure 3E:
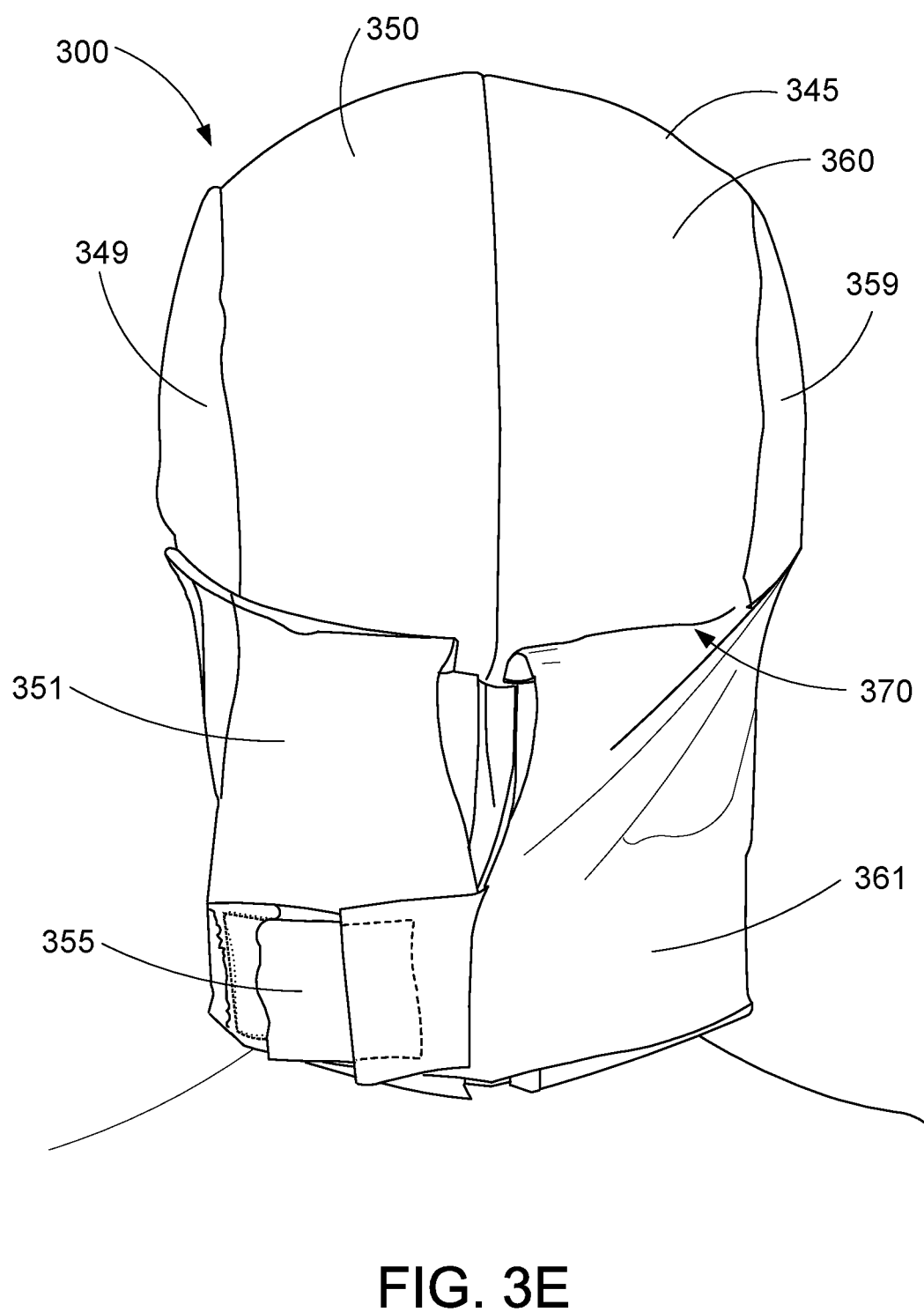
Figure 4A:
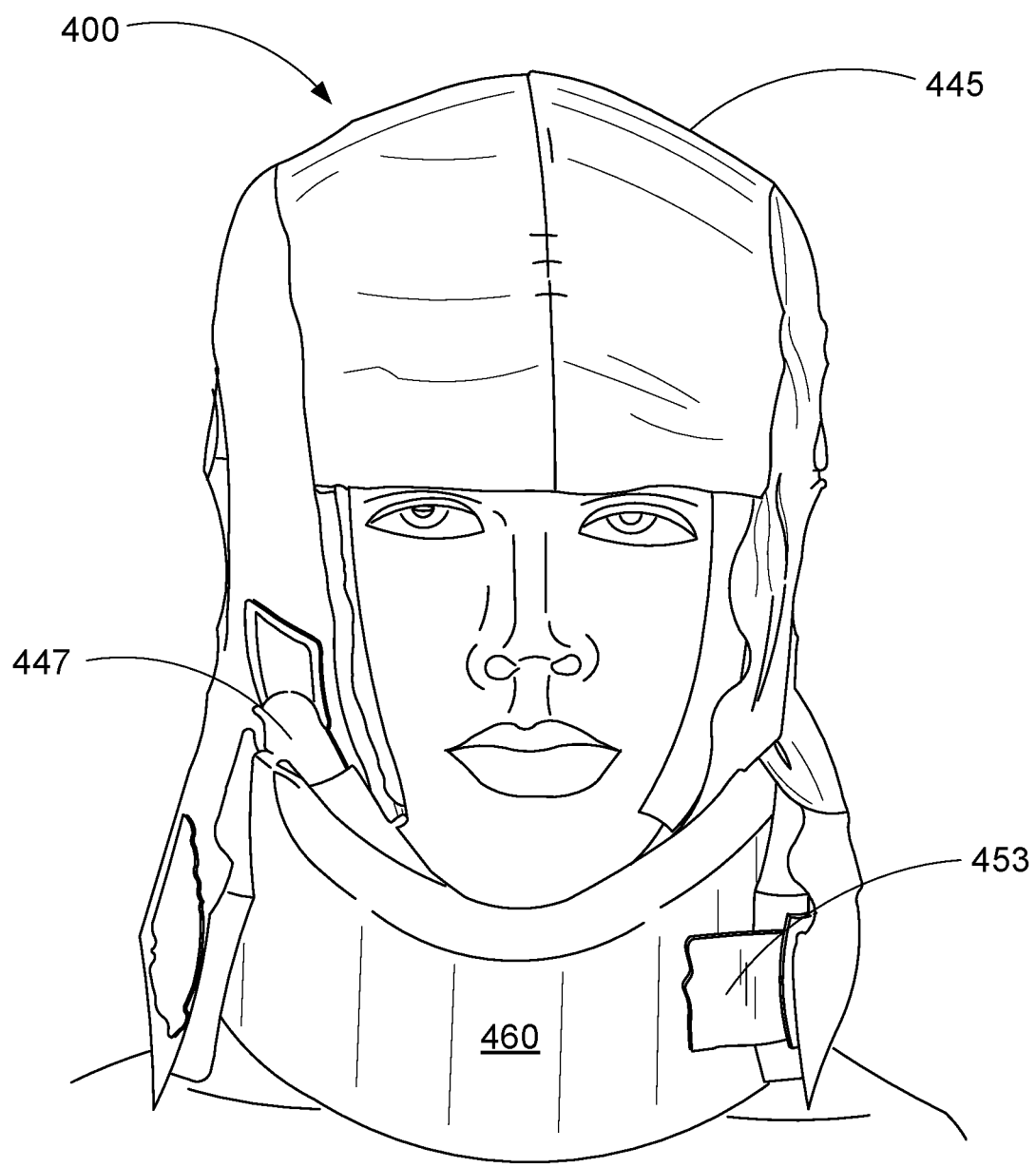
FIG. 4A-4D are front, front perspective, rear, and rear perspective views, respectively, of an embodiment of a cerebral protection system of the present disclosure with a cover and collar.
Figure 4B:
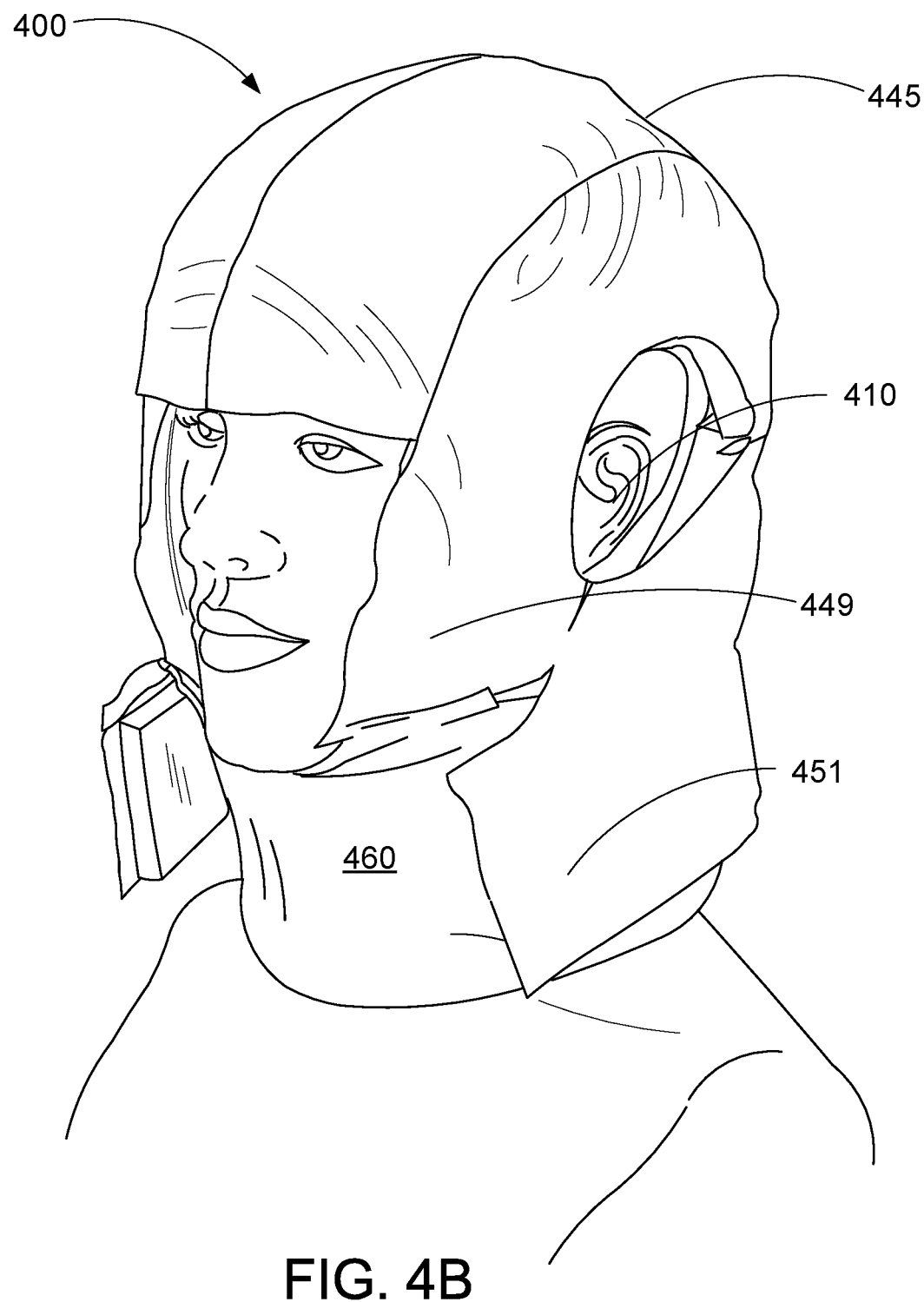
Figure 4C:
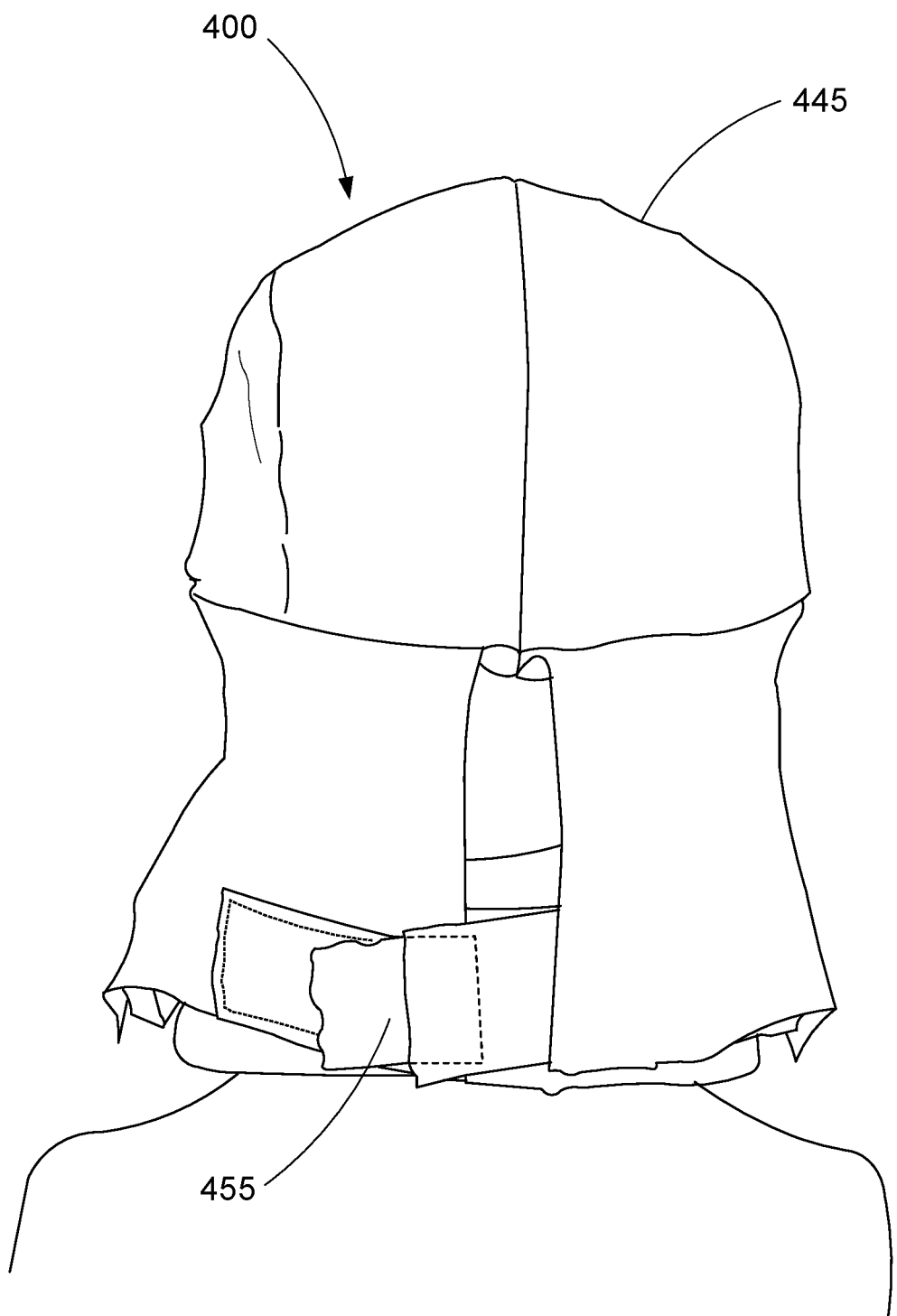
Figure 4D:
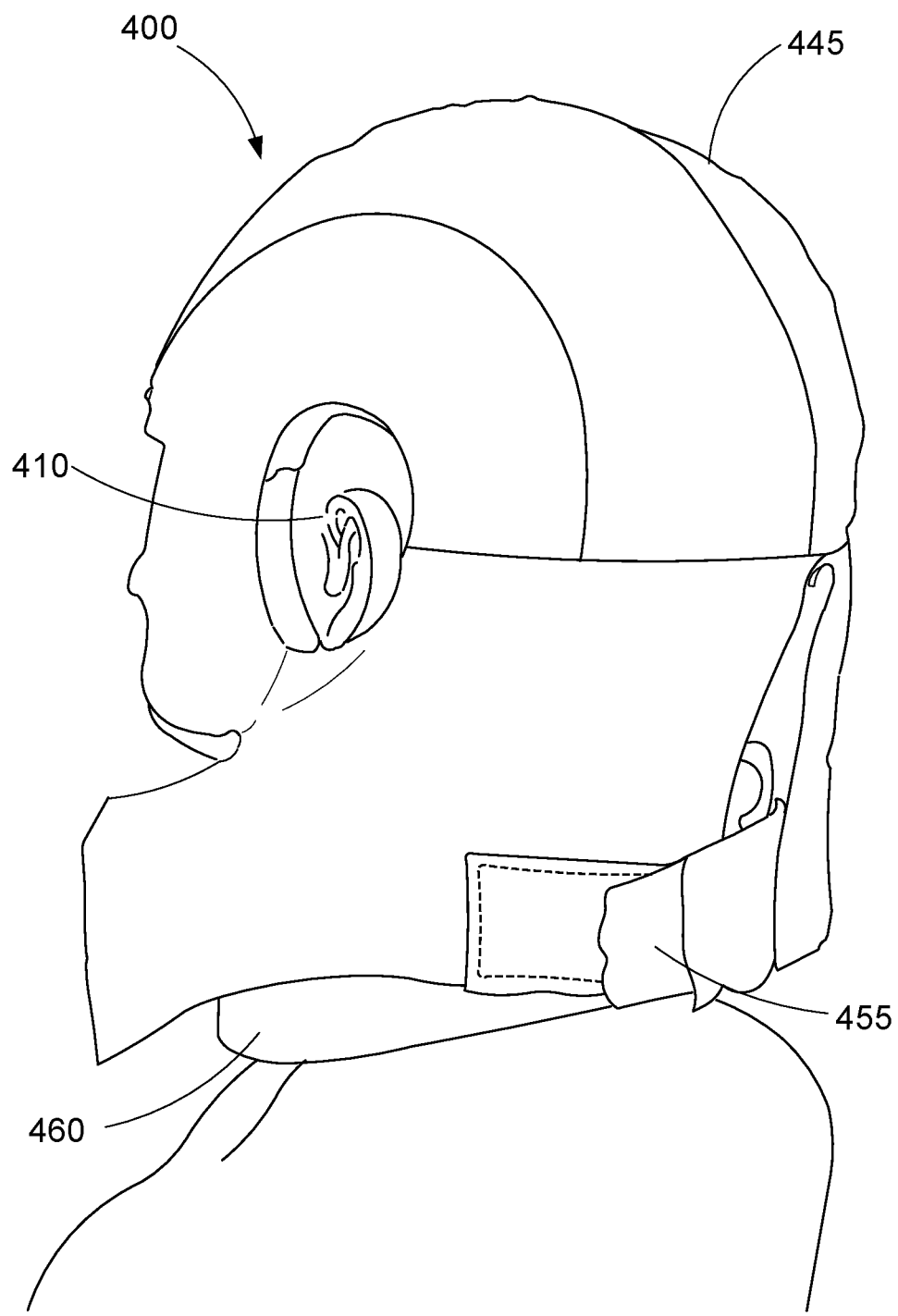
Figure 5A:
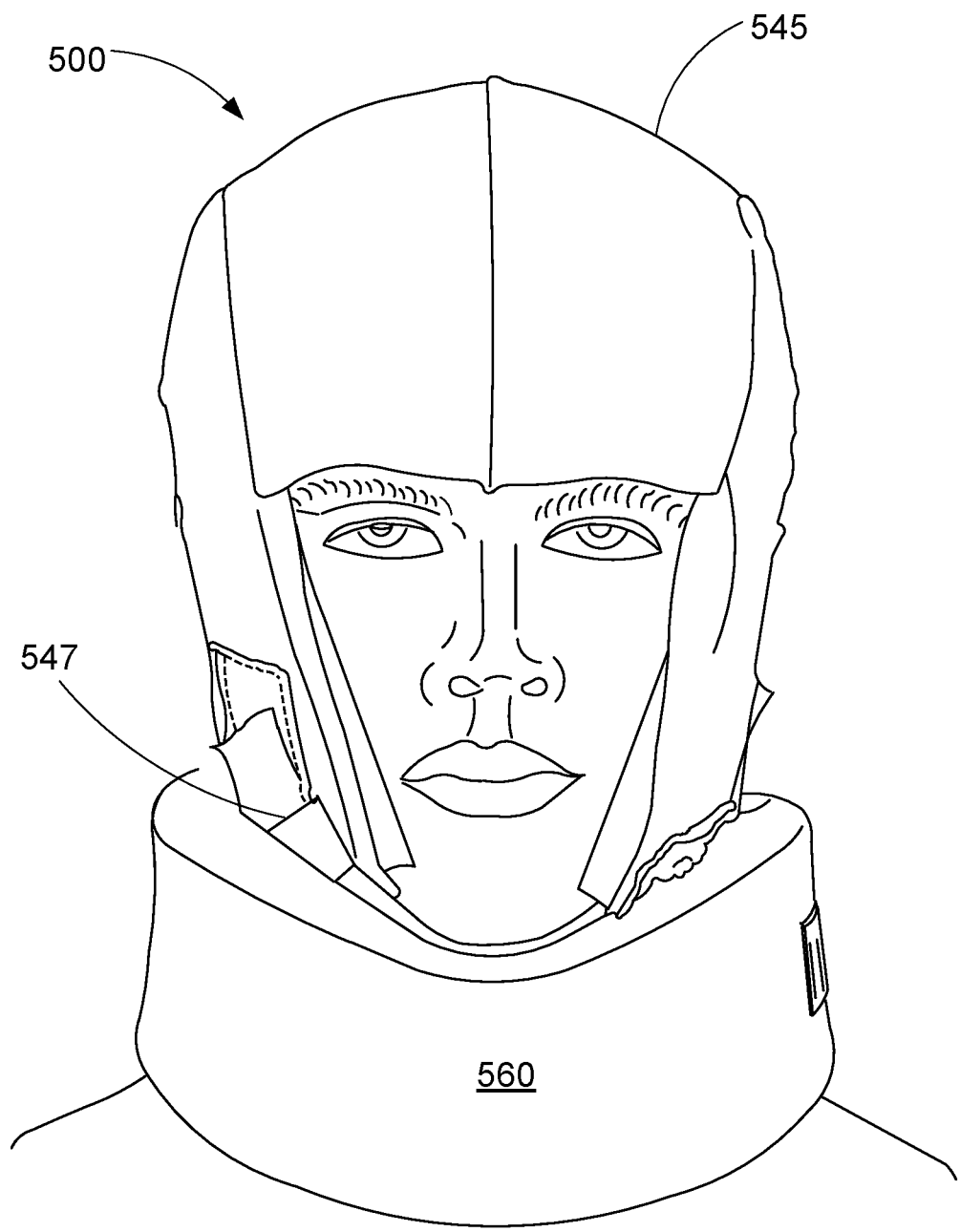
FIG. 5A-5D are front, side, rear perspective, and rear views, respectively, of an embodiment of a cerebral protection system of the present disclosure with a cover and a collar.
Figure 5B:
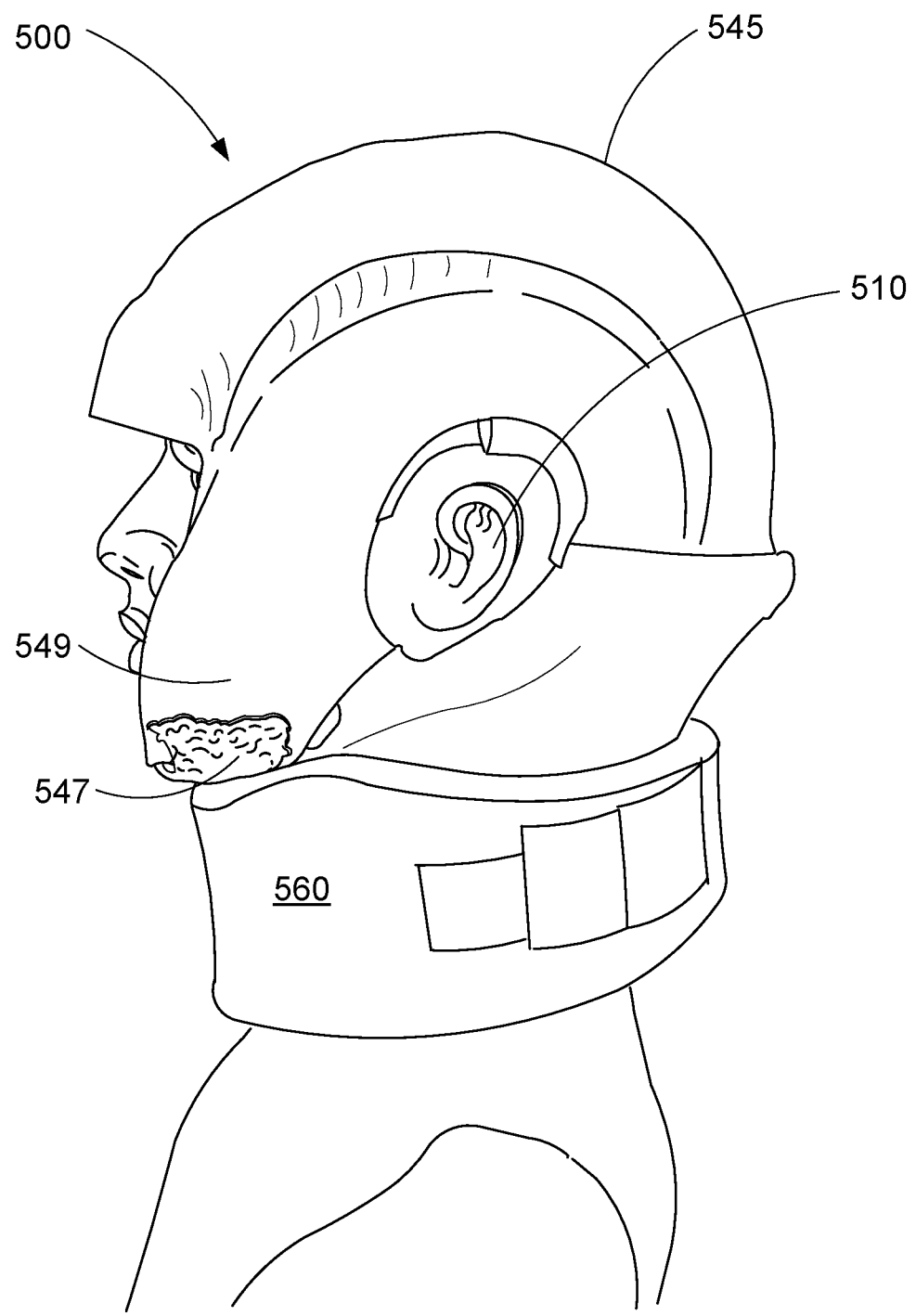
Figure 5C:
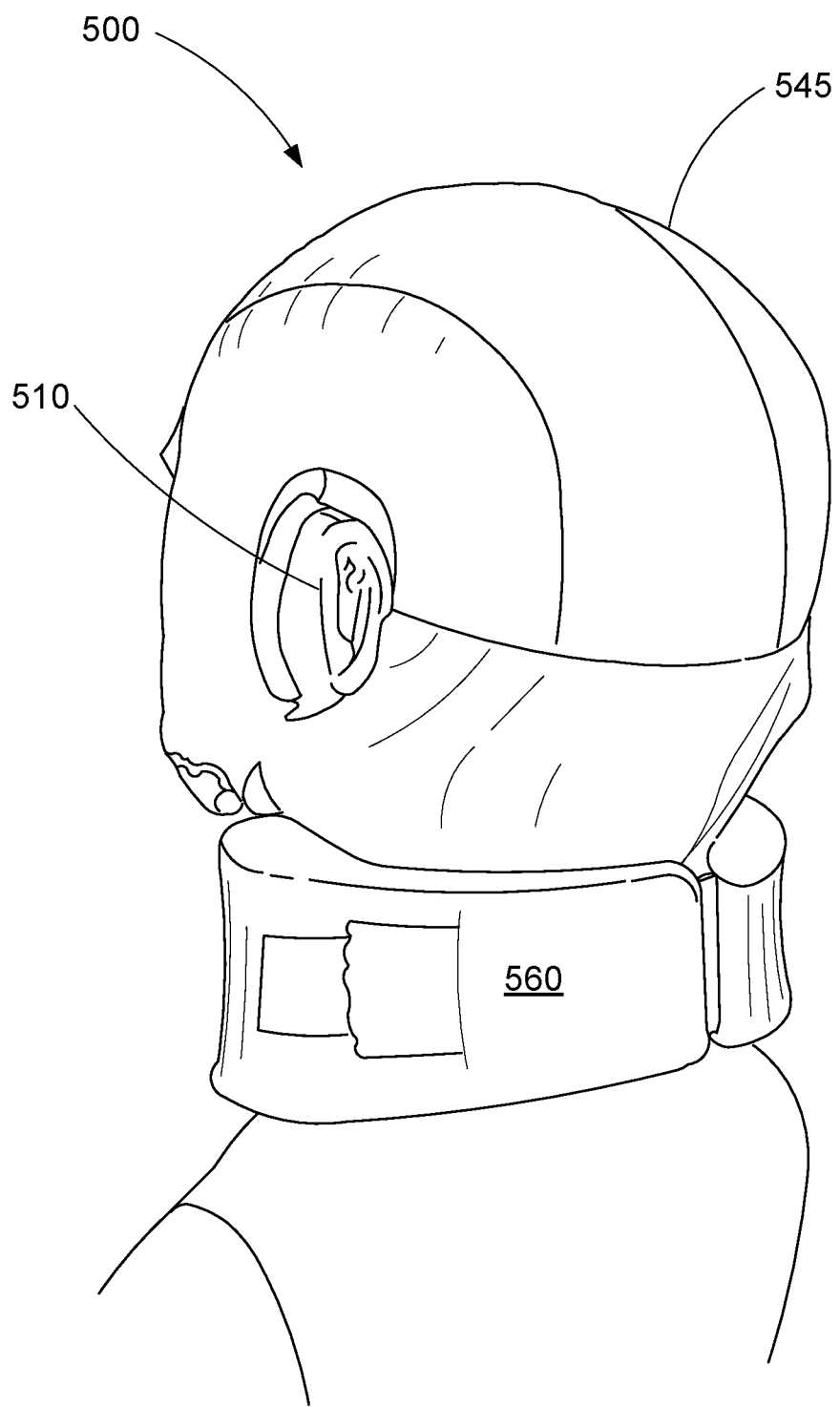
Figure 5D:
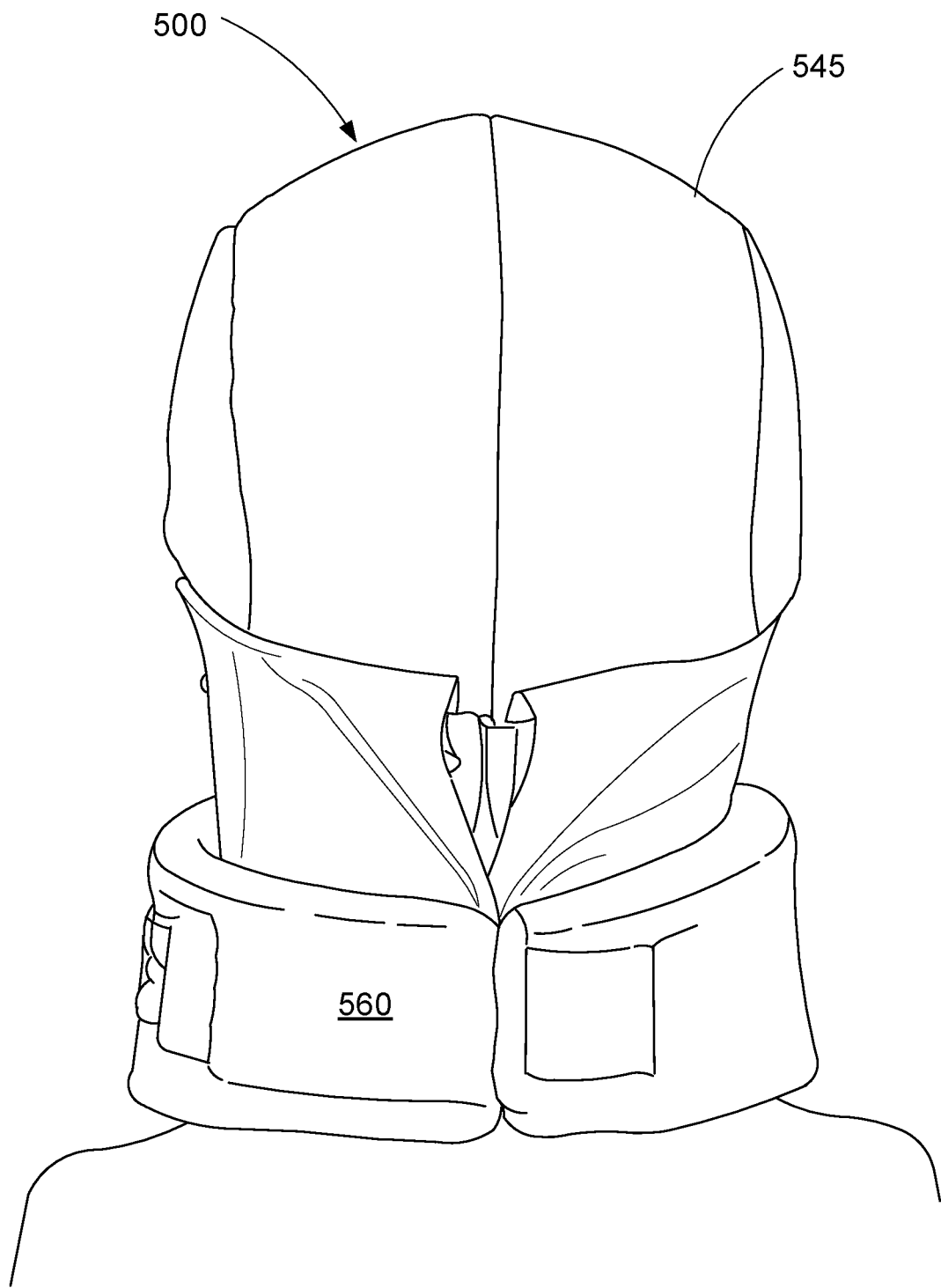

As best seen in FIG. 3C, the chin fastener 347 and the neck fastener 353 reside in perpendicular planes when the cerebral protection system 300 is secured to a patient's head. As best seen in FIG. 3E, all of the panels 349, 350, 351, 359, 360, 361 meet along a horizontal seam at the rear of the head. it is contemplated that the two neck cover portions 351, 361 are not joined together, but rather form an open vertical seam that runs up to the horizontal seam. Instead, the two neck cover portions are joined by the rear neck fastener 355. As seen later, this permits long hair to be passed outside of the insulating cover 345.

FIGS. 4A-4D illustrate the flexibility of the cerebral protection system 400 of the present disclosure. The cerebral cooling system 400 includes an insulating cover 445 including a cheek cover portion 449 and a neck cover portion 451, chin fastener 447, neck fastener 453, rear fastener 455, and ear holes 410. Also visible is a neck collar 460, which is used for protecting the neck and spinal cord (e.g., during transport of a patient from an injury site to a hospital). As seen here, the neck fastener 453 can be opened to permit the neck collar 460 to fit beneath the cerebral cooling system 400. Alternatively, the neck collar 460 can also be a cold pack and used to cool the brain. The carotid artery runs near the surface of the neck and the blood may be more easily cooled at the neck.

FIGS. 5A-5D illustrate another means of using the cerebral protection system. Here, the cerebral protection system 500 again includes an insulating cover 545 including a cheek cover portion 549, chin fastener 547, and ear holes 410. Here, the neck collar 560 is applied externally to the cerebral protection system 500. Here, the cerebral protection system is contemplated as being sized to be able to fit between the person's neck and the neck collar.

Figure 6A:
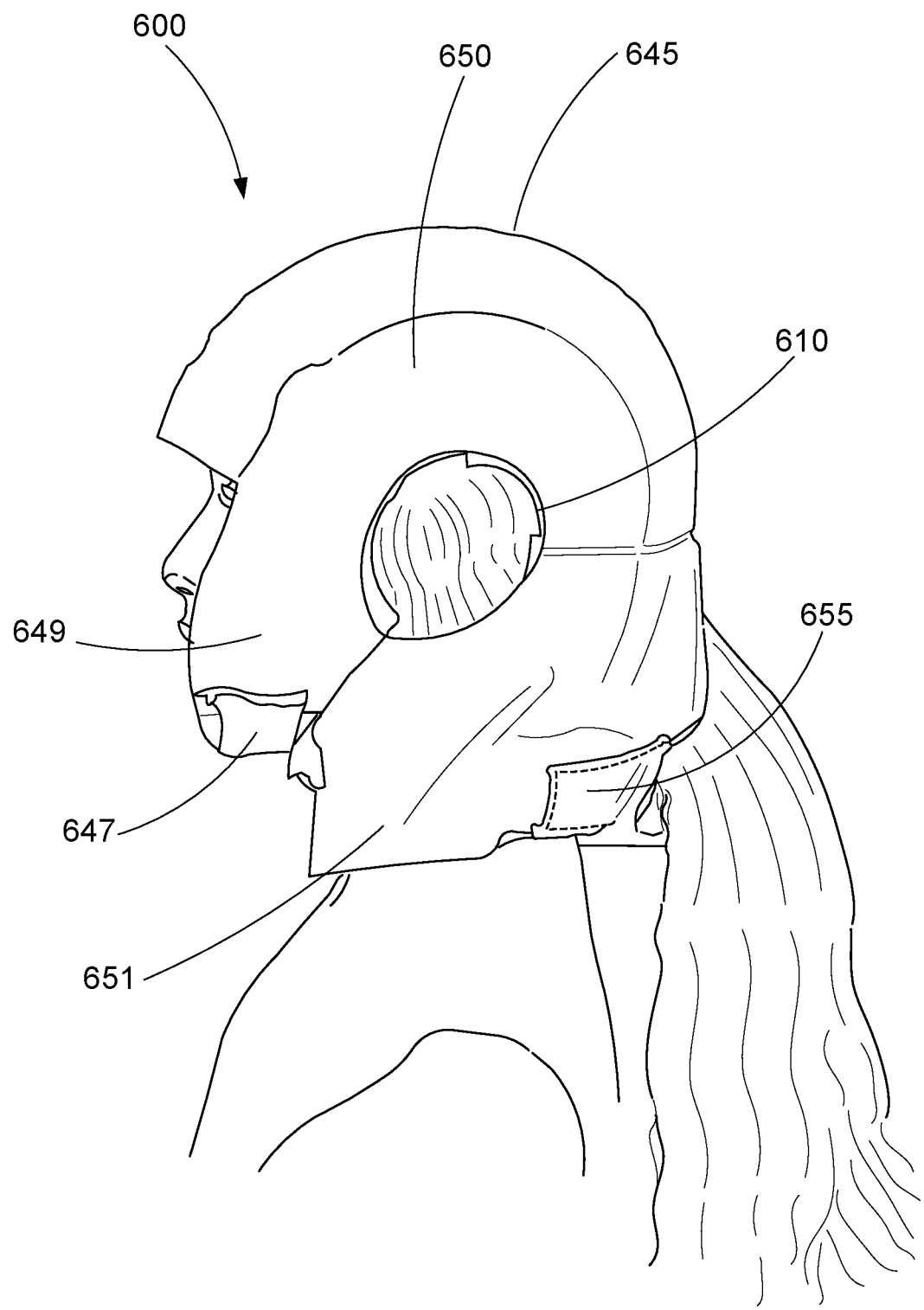
FIGS. 6A and 6B are side and rear views, respectively, of an embodiment of a cerebral protection system of the present disclosure which illustrate how the system may be applied to a patient who has a ponytail.
Figure 6B:
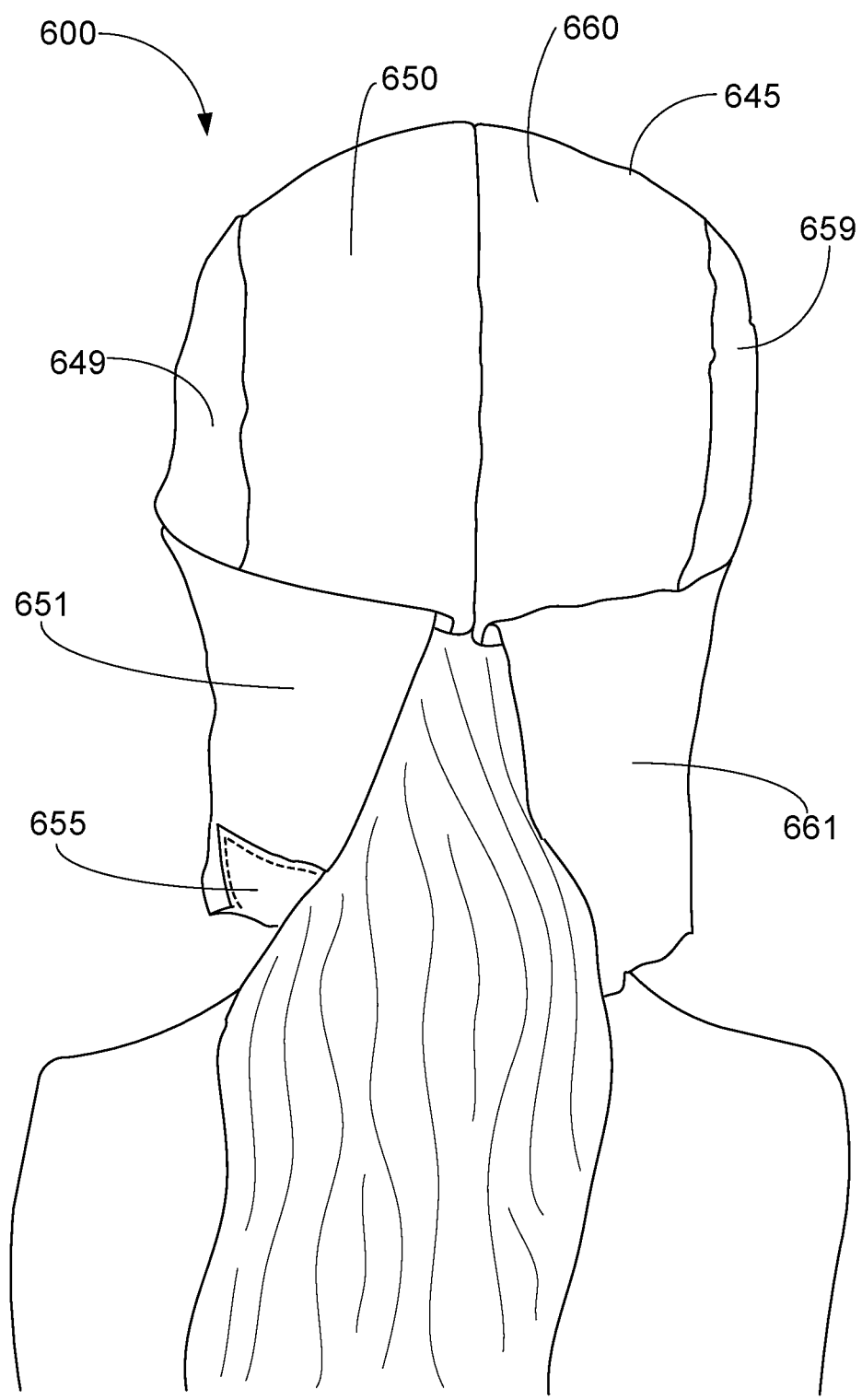

FIGS. 6A and 6B illustrate the cerebral protection system 600 being used on a person with long hair. The cover 645 includes left cheek cover portion 649, left top cover portion 650, left neck cover portion 651, right cheek cover portion 659, right top cover portion 660, and right neck cover portion 661. The cerebral protection system 600 also includes a chin fastener 647 for securing cold packs (beneath the cover 645, not shown) in an appropriate arrangement. As seen here, the open seam between neck cover portions 651, 661 and loosening of the rear neck fastener 655 permit a ponytail to extend through the cover 645.

Figure 7:
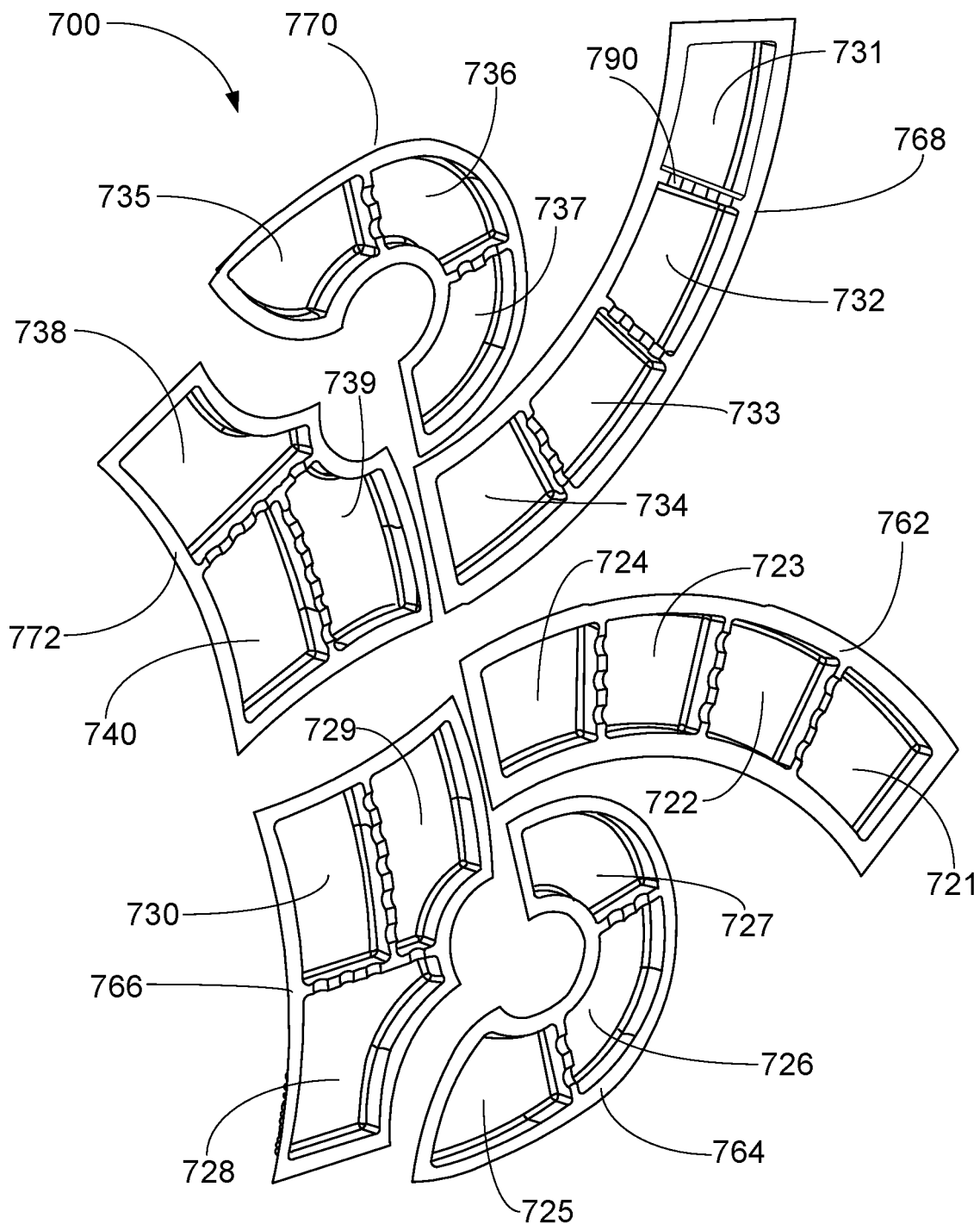
FIG. 7 illustrates an array of cooling packs which may be used in embodiments of a cerebral protection system of the present disclosure.

FIG. 7 show the set of trays which can also be used with the cerebral protection system 700. The set includes six trays 762, 764, 766, 768, 770, 772. Each tray includes an open top, a bottom surface, and a plurality of compartments separated by walls 790. It is contemplated that a cold pack is placed within each compartment. As seen here, the walls are scalloped to permit easier grasping of the cold pack in the compartment. The trays can be made of a soft, pliable material. In some embodiments, the tray material is a good heat conductor.

The first tray 762 is shaped to cover a top portion of the head and includes four compartments 721, 722, 723, and 724. The second tray 764 is shaped to cover a cheek and above-ear portion of the head and includes three compartments 725, 726, and 727. The third tray 766 is shaped to cover a neck and below-ear portion of the head and includes three compartments 728, 729, and 730.

The fourth tray 768 is shaped to cover a top portion of the head and includes four compartments 731, 732, 733, and 734. The fifth tray 770 is shaped to cover a cheek and above-ear portion of the head and includes three compartments 735, 736, and 737. The sixth tray 772 is shaped to cover a neck and below-ear portion of the head and includes three compartments 738, 739, and 740.

The first tray 762 is a reflection of the fourth tray 768. Put another way, if the first tray was held up to a mirror, the reflection would be in the shape of the fourth tray. Similarly, the second tray 764 is a reflection of the fifth tray 770, and the third tray 766 is a reflection of the sixth tray 772.

The first tray 762 and the fourth tray 768 can be described as having an arcuate shape covering an arc. The second tray 764 and the fifth tray 770 can be described as having an outer perimeter that extends about three-quarters of the circumference of a circle, and surrounding a central cutout. The third tray 766 and the sixth tray 772 can be described as being of a rectangular shape, with one corner being shaped to include an arc that completes the central cutout. The central cutout forms an earhole.

In some embodiments, it is contemplated that cold packs are placed within each compartment of the set of trays. For example, the cold packs seen in FIG. 2B would be placed within the trays seen in FIG. 7. Each cold pack contains the two different reactive materials separated by a rupturable membrane, which react endothermically when mixed. In these embodiments, the trays can be fastened to the insulating cover, so that the cold packs directly contact the patient's head. Alternatively, the trays can be fastened to the insulating cover such that the cold packs are trapped between the bottom of the tray and the insulating cover, and the tray bottom directly contacts the patient's head. In these embodiments, the tray material should be a good heat conductor. Thus, for example, the first tray 768 may cover either the top right portion of the head, or the top left portion of the head, depending on how the cold packs and trays are arranged.

In some other embodiments, the reactive materials can be placed within the tray compartments, and the top of the tray would be sealed with a film. Adjacent compartments would contain different reactive materials and be isolated from each other. For example, the passageways 790 in FIG. 7 would be sealed by rupturable membranes. When the membranes are ruptured, the reactive materials would be mixed and react endothermically. The materials include two or more reactants and/or catalysts. For example, in a tray including three compartments, each compartment may contain a different reactive material or catalyst, permitting the reaction to occur or to speed up the rate of the reaction.

In some embodiments, both of the reactive materials are present in a single compartment, but the reaction kinetics are such that very little heat is absorbed. In an adjacent compartment separated by a rupturable membrane, a catalyst is present which increases the reaction rate sufficiently to absorb enough heat to selectively create a hypothermic effect in at least a portion of a patient's brain upon rupture of the membrane.

The cover may include a thin outer layer and an inner insulation layer. The outer layer may be comprised of suitable materials. The insulation layer includes one or more insulating materials. The insulating cover would be attached to the trays using known fasteners or similar means.

The reactive materials causing the endothermic reaction are, in particular embodiments, water and ammonium chloride. Other combinations of materials that result in an endothermic reaction include water with ammonium nitrate; water with potassium chloride; and ethanoic acid with sodium carbonate.

As illustrated here, a total of 20 cold packs and six trays are used to make the cerebral protection system. The number of cold packs, and the number of trays, can be varied as desired. The number of compartments in each tray can also be varied as desired.

The membranes in different trays may be ruptured independently. In other words, the endothermic reaction may be selectively induced in specific parts of the cerebral protection system. Selective rupturing of the membranes permits control of which areas of the brain (e.g., frontal, parietal, temporal, or occipital regions) are cooled. For example, to prevent/minimize damage to the left prefrontal cortex, membranes could be selectively ruptured on the top and front of the cerebral protection system on the left side that will be adjacent to the relevant portion of a patient's skull when the system is in use.

The fasteners described herein may be of any type of fastener including, but not limited to, hook and loop-type fasteners.

The cerebral protection system is in the shape of a helmet. Typically, patients with head trauma are lying down on a flat surface. It is contemplated that the insulating cover can be opened and then slid underneath the patient's head, then sealed together using the fasteners. If desired, the insulating cover can be made in two separate pieces and then joined together with a large fastener across the top of the insulating cover.

It is also contemplated that in some embodiments, the inner surface of the insulating cover contacting the patient's head may contain pouches that are shaped and arranged to hold cold packs in locations corresponding to those described for the compartments in the trays. Some pouches are located to cover a top portion of the head, similar to the first tray and the four tray, and cover an arc. Some pouches are located to cover a cheek and above-ear portion of the head, like the second tray and the fifth tray, and together have an outer perimeter that extends about three-quarters of the circumference of a circle, and surrounds a central cutout. Some pouches are located to cover a neck and below-ear portion of the head, like the third tray and the sixth tray, and together have a rectangular shape, with one corner being shaped to include an arc that completes the central cutout. The central cutout forms an earhole.

The cerebral protection system of the present disclosure has several indications of use, or conditions which can be positively treated using the system. These conditions can be treated by applying the cerebral protection system to the head of a patient experiencing the condition. Such conditions include concussion; traumatic brain injury (TBI); heatstroke; after cardiac arrest; after respiratory arrest; anoxic brain injury (e.g. caused by respiratory arrest); ischemic stroke; transient ischemic attack (TIA); and hypoxic ischemic encephalopathy (which can lead to cerebral palsy in infants). Generally, reducing metabolic activity is helpful in extending the time to obtain treatment for these conditions, or reducing temperature is a means for treating such a condition. Concussions and concussion-like symptoms can be caused by a blow to the head, or by exposure to radio frequencies such as microwaves, or exposure to sonic waves. Traumatic brain injury is a broader category of injuries that can occur due to blows or jolts to the head, including both physical contact (e.g. a first hitting the head) and non-physical contact (e.g. shock wave or overpressure from an explosion). The cerebral protection system is applied for a suitable time period as desired.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:

1. A method for reducing metabolic activity of a patient, comprising:
   applying a cerebral protection system to the head of the patient, wherein the cerebral protection system comprises:
      an array of cold packs shaped to cover the head, each cold pack containing a first reactive material, a second reactive material, and a rupturable membrane separating the first reactive material from the second reactive material;
      wherein the first reactive material and the second reactive material are capable of mixing and reacting in an endothermic reaction when the rupturable membrane is ruptured;
      an insulating cover; and
      a plurality of trays, each tray comprising an open top, a bottom, a plurality of compartments therein, and walls separating the compartments, wherein each compartment is configured to receive a cold pack, and where each tray is configured for attachment to the insulating cover.

2. The method of claim 1, wherein the first reactive material is water and the second reactive material is ammonium chloride.

3. The method of claim 1, wherein the insulating cover includes a neck fastener shaped to extend from one side of the neck to the other side of the neck.

4. The method of claim 1, wherein the insulating cover includes a chin fastener shaped to extend from a first area adjacent a first cheek of the head below a chin of the head to a second area adjacent a second cheek of the head.

5. The method of claim 1, wherein a rear of the insulating cover includes an open vertical seam.

6. The method of claim 1, wherein each tray fastens to the insulating cover such that the plurality of cold packs is located between the insulating cover and the bottom of the tray.

7. The method of claim 1, wherein the plurality of trays comprises:
   a first tray and a fourth tray which are reflections of each other;
   a second tray and a fifth tray which are reflections of each other; and
   a third tray and a sixth tray which are reflections of each other;
   wherein the first tray, second tray, third tray, fourth tray, fifth tray, and sixth tray each contain a plurality of compartments;
   wherein the first tray has an arcuate shape;
   wherein the second tray has an outer perimeter that extends about three-quarters of the circumference of a circle, and surrounds a central cutout;
   wherein the third tray has a rectangular shape with one corner being shaped to include an arc that cooperates with the second tray to complete the central cutout and form an earhole; and
   wherein each tray compartment contains a cold pack.

8. A method for treating concussion, traumatic brain injury (TBI), heatstroke, cardiac arrest, respiratory arrest, anoxic brain injury, ischemic stroke, transient ischemic attack (TIA), or hypoxic ischemic encephalopathy in a patient, comprising:
   applying a cerebral protection system to the head of the patient, wherein the cerebral protection system comprises:
      an array of cold packs shaped to cover the head, each cold pack containing a first reactive material, a second reactive material, and a rupturable membrane separating the first reactive material from the second reactive material,
      wherein the first reactive material and the second reactive material are capable of mixing and reacting in an endothermic reaction when the rupturable membrane is ruptured;
      an insulating cover; and
      a plurality of trays, each tray comprising an open top, a bottom, a plurality of compartments therein, and walls separating the compartments, wherein each compartment is configured to receive a cold pack, and where each tray is configured for attachment to the insulating cover.

9. The method of claim 8, wherein the first reactive material is water and the second reactive material is ammonium chloride.

10. The method of claim 8, wherein the insulating cover includes a neck fastener shaped to extend from one side of the neck to the other side of the neck.

11. The method of claim 8, wherein the insulating cover includes a chin fastener shaped to extend from a first area adjacent a first cheek of the head below a chin of the head to a second area adjacent a second cheek of the head.

12. The method of claim 8, wherein a rear of the insulating cover includes an open vertical seam.

13. The method of claim 8, wherein the plurality of trays comprises:
   a first tray and a fourth tray which are reflections of each other; a second tray and a fifth tray which are reflections of each other; and a third tray and a sixth tray which are reflections of each other; wherein the first tray, second tray, third tray, fourth tray, fifth tray, and sixth tray each contain a plurality of compartments;
   wherein the first tray has an arcuate shape;
   wherein the second tray has an outer perimeter that extends about three-quarters of the circumference of a circle, and surrounds a central cutout;
   wherein the third tray has a rectangular shape with one corner being shaped to include an arc that cooperates with the second tray to complete the central cutout and form an ear hole; and
   wherein each tray compartment contains a cold pack.

14. The method of claim 8, wherein the concussion is caused by a blow to the head, or exposure to radio frequencies, or exposure to sonic waves.

* * * * *